US00PP16541P2

(12) United States Plant Patent
Olesen

(10) Patent No.: US PP16,541 P2
(45) Date of Patent: May 16, 2006

(54) HYBRID TEA ROSE PLANT NAMED 'POULREN013'

(50) Latin Name: ***Rosa* hybrid**
Varietal Denomination: Poulren013

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 73 days.

(21) Appl. No.: 11/002,529

(22) Filed: Dec. 1, 2004

(51) Int. Cl.
*A01H 5/00* (2006.01)

(52) U.S. Cl. ..... Plt./138
(58) Field of Classification Search ..... Plt./138, Plt./137, 107
See application file for complete search history.

*Primary Examiner*—Anne Marie Grunberg
*Assistant Examiner*—June Hwu

(57) ABSTRACT

A new garden rose plant of the hybrid tea class which has abundant, pink flowers and attractive foliage. This new and distinct variety has shown to be uniform and stable in the resulting generations from asexual propagation.

3 Drawing Sheets

Botanical classification: *Rosa* hybrid.
Variety denomination: 'Poulren013'.

The present invention constitutes a new and distinct variety of garden rose plant which originated from a controlled crossing between the female parent plant, a variety by the same inventors named 'Poulsyng', described and illustrated in U.S. Plant patent application Ser. No. 09/268,299 dated Mar. 16, 1999 (now abandoned), and the male parent, an unnamed seedling. The two parents were crossed during the summer of 1996 and the resulting seeds were planted in a controlled environment in Fredensborg, Denmark. The new variety is named 'Poulren013'.

The new variety may be distinguished from its female seed parent, 'Poulsyng' by the following combination of characteristics:

1. Flower petal color of 'Poulsyng' is Red Group 36D, while 'Poulren013' is Red-Purple Group 65A to 65B.
2. 'Poulsyng' has 34 to 40 petals 'Poulren013' normally has 50 petals.

The new variety may be distinguished from its pollen parent, an unnamed seedling, by the following combination of characteristics:

1. 'Poulren013' has Yellow basal petal spots, while the pollen parent has no distinctive coloration at the base of the petal.
2. Flowers of the new variety have a much stronger fragrance than those of the pollen parent.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots;
3. Disease resistance;
4. Exceptional flower fragrance;
5. Attractive, dark green foliage.

This combination of qualities is not present in previously available commercial cultivars of this type, known to the inventors, and distinguish 'Poulren013' from all other varieties of which we are aware.

As part of the rose development program, Mogens N. Olesen germinated the seeds from the aforementioned hybridization during winter of 1996 and conducted evaluations on the resulting seedlings in a controlled environment in Fredensborg, Denmark.

'Poulren013' was selected in the spring 1997 by the inventors as a single plant from the progeny of the aforementioned hybridization.

Asexual reproduction of 'Poulren013' by traditional budding and rooted cuttings was first done by Mogens N. Olesen in the nursery in Fredensborg, Denmark in July, 1997. This initial and other subsequent asexual propagations conducted in controlled environments have demonstrated that the characteristics of 'Poulren013' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulren013'. Specifically illustrated in SHEET 1, SHEET 2 AND SHEET 3:

FIG. 1.1; Open flower above view;

FIG. 1.2; Open flower side view with attachment of receptacle, sepals, and peduncle;

FIG. 1.3; Sepals, reproductive organs, receptacle, and pedicel.

FIG. 1.4; Flower petals, detached;

Specifically illustrated in SHEET 2:

FIG. 2.0; Cluster of flower buds showing attachment to stem and leaves;

Specifically illustrated in SHEET 3:

FIG. 3.1; Juvenile leaves exhibiting anthocyanin;
FIG. 3.2; Mature leaf;
FIG. 3.3; Mature stem exhibiting thorns;
FIG. 3.4; Mature leaf.

DETAILED DESCRIPTION OF THE VARIETY

The following is a description of 'Poulren013', as observed in its growth in a field nursery in Jackson County, Oreg. Observed plants are 3 years of age. Plants were grown on *Rosa multiflora* understock. Color references are made using The Royal Horticultural Society (London, England)

Colour Chart, 1995, except where common terms of color are used.

For a comparison, several characteristics of a Patented rose variety named 'Wekuz', described and illustrated in U.S. Plant Pat. No. 8,183 issued Mar. 23, 1993 are compared to 'Poulren013' in Chart 1.

CHART 1

| | 'Poulren013' | 'Wekuz' |
|---|---|---|
| Inside petal surface color | White Group 155A at basal zone blending with Red-Purple Group 65A and 65B | Red Purple 65A |
| Petalage | 50 petals | 20 to 30 |
| Flower diameter | 85 mm | 80 to 100 mm |

FLOWER AND FLOWER BUD

Blooming habit: Recurrent.

Flower bud:

*Size.*—Upon opening, 27 mm in length from base of receptacle to end of bud. Bud diameter is 16 mm.

*Bud form.*—Urceolate.

*Bud color.*—As sepals unfold, petals are Yellow-White Group 158B with intonations of Red-Purple Group 58D and a blend of Greyed-Purple Group 184D and Red-Purple 58C Group.

*Sepal inner surface.*—Color: Yellow-Green 148C. Surface: Strongly pubescent.

*Sepal outer surface.*—Color: Yellow-Green Group 144A. Anthocyanic pigments the color of Greyed-Purple Group 183B observed. Texture: Smooth.

*Sepal shape.*—Subulate. Apex: Cirrhose. Base: Flat at union with receptacle.

*Sepal margin.*—Margins have weak foliaceous appendages on three of the five sepals.

*Sepal size.*—30 mm (l)×10 mm (w).

*Receptacle.*—Texture: Smooth. Shape: Urn-shaped. Size: 10 mm (l)×10 mm (w). Color: Yellow-Green Group 144A.

*Pedicel.*—Length: 35 to 40 mm. Diameter: 3 mm. Color: Yellow-Green Group 144A with anthocyanic pigments Greyed-Orange Group 173A.

Flower bud development: Flower buds are borne in clusters of 5 to 10 flower buds per stem.

Flower bloom:

*Fragrance.*—Very strong, perfume scent.

*Duration.*—The blooms have a duration on the plant of approximately 10 to 13 days. Petals do not fall cleanly away from plant after flowers have matured.

*Size.*—Flower diameter is 85 mm when open. Flower depth is normally 45 mm.

*Flower shape.*—Upon opening petals form tight globular centers. After opening, petals curve out from the center forming a cup.

*Shape of flower, side view.*—Upon opening, Upper portion: Flattened convex. Lower portion: Concave. After opening, Upper portion: Flat. Lower portion: Concave.

Petalage: Under normal conditions, flowers have 50 petals total, 10 of which are petaloids.

Flower petal color:

*Upon opening, outer petals.*—Upper and lower surface: Basal zone is White Group 155A becoming Red-Purple Group 65A to 65B at the middle and marginal zone.

*Upon opening, inner petals.*—Upper surface: Basal Zone is White Group 155A, becoming Red-Purple Group 65A at the middle and marginal zone. At margins petals are Red-Purple Group 67D. Lower surface: Basal zone is White Group 155A blending with Red-Purple Group 65A and 67D at middle and marginal zones.

*Basal petal spots, upon opening.*—Upper surface: Yellow Group 4A. Lower surface: Yellow Group 4D.

*After opening, outer petals.*—Upper surface: White Group 155A at basal zone blending with Red-Purple Group 65A and 65B at middle and marginal zones. Occasionally vertical streaking of Red-Purple Group 65D observed. Lower surface: White 155A at basal zone blending with Red-Purple Group 65A and 65B at mid and marginal zones. Occasionally vertical streaking of Red-Purple Group 65D in color observed.

*After opening, inner petals.*—Upper surface: White Group 155A at basal zone blending with Red-Purple Group 65A and 65B at middle and marginal zones. Occasionally vertical streaking of Red-Purple Group 65D observed. Lower surface: White 155A at basal zone blending with Red-Purple Group 65A and 65B at mid and marginal zones. Ocasionally vertical streaking of Red-Purple Group 65D in color observed.

*Basal petal spots, after opening.*—Upper surface: Yellow Group 4C. Lower surface: Yellow Group 4D.

General tonality: On open flowers, Red-Purple Group 61D towards flower center becoming Red-Purple Group 65B at the outer petals. No change in the general tonality at the end of the $10^{th}$ day. Afterwards, general tonality is Red-Purple Group 62B at center and Red-Purple Group 69C at the outer petals.

Petals:

*Petal reflex.*—Moderate reflexing occurs at the petal margins late in flower development, after flowers have fully matured.

*Margin.*—Entire. Weakly undulating.

*Shape.*—Generally narrow elliptical in shape. Apex: Rounded. Base: Acute.

*Outer petal size.*—45 mm (l)×40 mm (w).

*Inner petal size.*—40 mm (l)×30 mm (w).

*Texture.*—Smooth.

*Thickness.*—Average.

Petaloids:

*Size.*—27 mm (l)×11 mm (w).

*Shape.*—Irregular and asymmetric.

*Color.*—Upper surface is White Group 155A at basal zone blending with Red-Purple Group 65A and 65B at middle and marginal zones. The lower surface is White 155A at basal zone blending with Red-Purple Group 65A and 65B at the middle and marginal zones. Basal petal spots on the upper and lower surfaces are Yellow Group 4C to 4D.

Reproductive organs:

*Pollen.*—None observed.

*Anthers.*—Size: 3 mm in length. Color: Greyed-Yellow Group 160D. Quantity: Normally 100.

*Filaments.*—Color: Yellow-Green Group 150D. Length: 7 to 10 mm.

*Pistils.*—Quantity: 60 on average.

*Stigmas.*—Superior in location relative to the length of the filaments and the height of the anthers. Color: Orange-White Group 159A.

*Styles.*—Color: Red-Purple Group 57A.

*Hips.*—None Observed in the field nursery in Jackson County Oreg.

PLANT

Plant growth: Upright to bushy with even growth. When grown as a budded field grown plant on *Rosa multiflora* understock, the average height of the plant is 100 to 150 cm.

Stems:

*Color.*—Juvenile growth: Yellow-Green Group 144B. Mature growth: Yellow-Green Group 144B.

*Length.*—On average, canes are 80 cm from the base of the plant to the flowering portion.

*Diameter.*—5 to 8 mm.

*Internodes.*—On mature canes, there is an average distance of 25 to 30 mm between nodes.

*Surface texture.*—Young wood: Smooth. Older wood: Smooth.

Thorns:

*Incidence.*—8 thorns per 10 cm of stem.

*Size.*—Average length of thorns on mature stems is 5 mm.

*Shape.*—Upper side: Convex. Lower side: Concave.

*Color.*—Juvenile thorns: Greyed-Red Group 178A. Mature thorns: Greyed-Red Group 178A.

Plant foliage: Normal number found on compound leaves in middle of the stem is 7 leaflets.

*Compound leaf.*—170 mm (l)×130 (w).

*Quantity.*—3 leaves per 10 cm of stem on average.

*Color of mature foliage.*—Upper side: Green Group 137A to 139A. Lower side: Green Group 138A and 138B blend.

*Color of juvenile foliage.*—Upper side: Yellow-Green Group 146C with anthocyanin Greyed-Purple Group 183B at margins and veins. Lower side: Yellow-Green Group 146C with anthocyanin throughout of Greyed-Purple Group 183B.

Plant leaves and leaflets:

*Stipules.*—Size: 20 mm in length. Shape: Linear, slightly broad based with outward extending apecies. Margins: Finely serrated with many stipitate glands. Color: Yellow-Green Group 144A.

*Petiole.*—Length: 25 mm. Diameter: 2 mm.

*Upper surface.*—Color: Greyed-Purple Group 184D.

*Lower surface.*—Color: Yellow-Green Group 144B. Observations: Stipitate glands and small prickles observed.

*Rachis.*—Length: 55 mm. Upper surface: Color: Yellow-Green Group 144A. Lower surface: Color: Yellow-Green Group 144B. Observations: Stipitate glands and small prickles observed.

*Leaflet.*—Edge: Serrated. Size: Average size of the terminal leaflet on normal leaves is 55 mm (l)×40 mm (w). Shape: Generally ovate. Base: Rounded. Apex: Acuminate. Texture: Smooth. Thickness: Thick. Arrangement: Odd pinnate. Venation: Reticulate. Glossiness: Moderately glossy.

Disease resistance: Above average resistance to powdery and downy mildew, rust, black spot, and *Botrytis* under normal growing conditions in Jackson County, Oreg.

Cold hardiness: The variety 'Poulren013' has been found to be cold tolerant to USDA Cold Hardiness Zone 6.

It is claimed:

1. A new and distinct variety of rose plant of the hybrid tea rose class named 'Poulren013', substantially as herein illustrated and described as a distinct and novel rose variety due to its abundant pink flowers, disease resistance, and extended period of bloom.

* * * * *

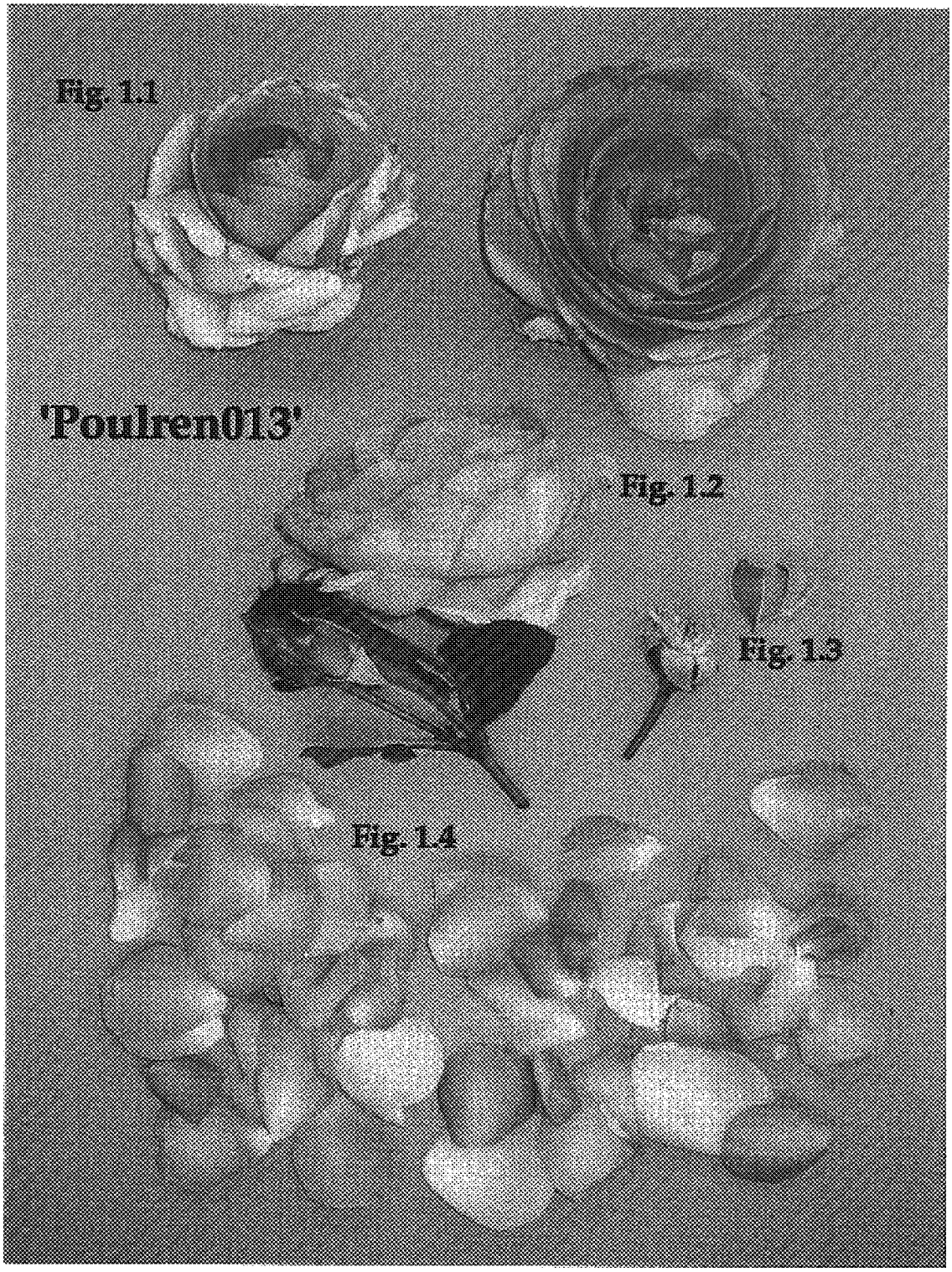
Fig. 1.1
'Poulren013'
Fig. 1.2
Fig. 1.3
Fig. 1.4

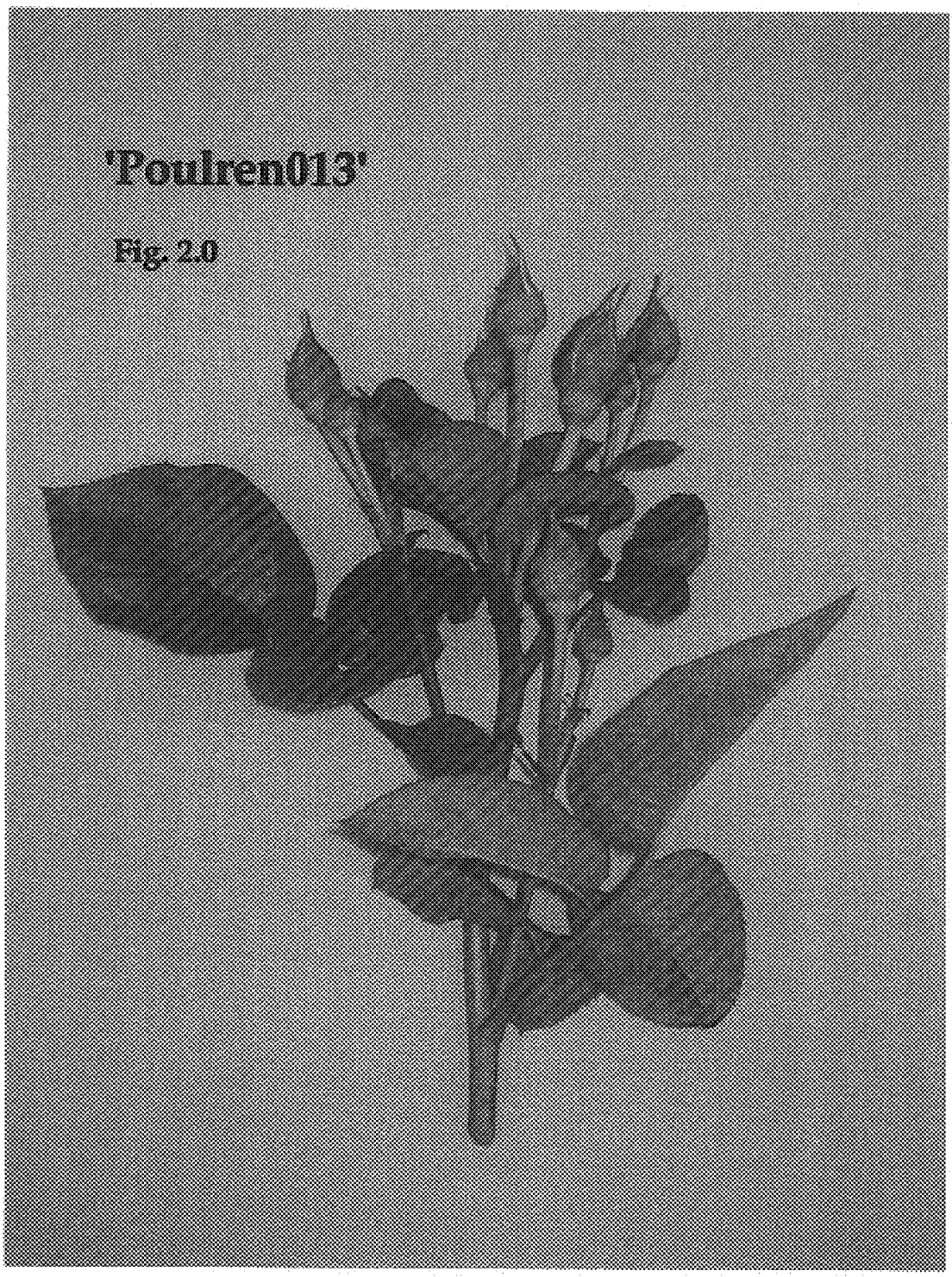
Fig. 2.0

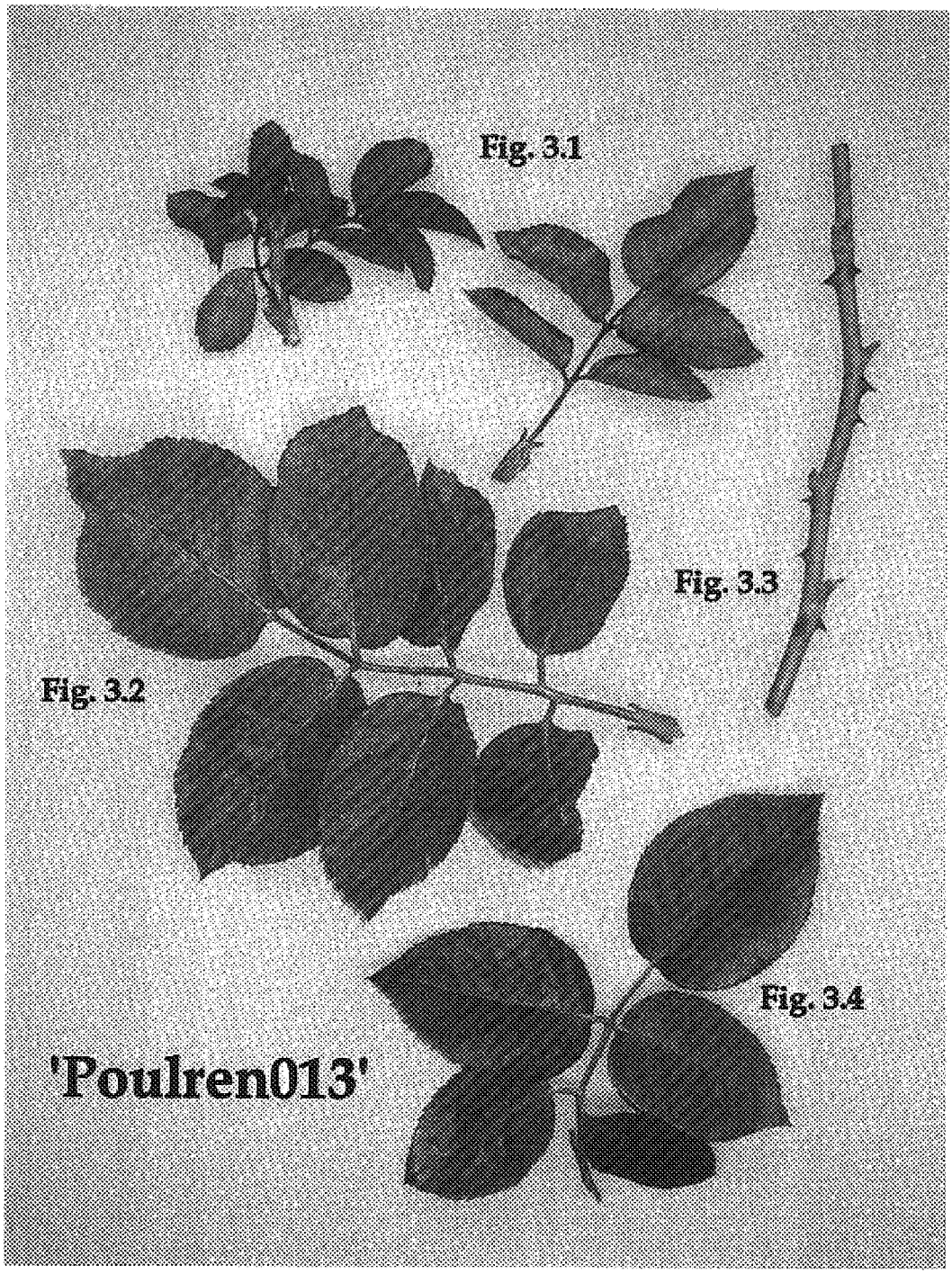
Fig. 3.1
Fig. 3.2
Fig. 3.3
Fig. 3.4
'Poulren013'